(12) United States Patent
Kolos et al.

(10) Patent No.: US 6,737,083 B2
(45) Date of Patent: May 18, 2004

(54) TOPICALLY APPLIED SYNTHETIC OCEAN WATER MIXTURE AND METHOD OF USING SAME

(76) Inventors: Edward Kolos, 1921 SW. 15th St. #32, Deerfield Beach, FL (US) 33442; Jeffrey D. Newsom, 1921 SW. 15th St. #32, Deerfield Beach, FL (US) 33442

( * ) Notice: Subject to any disclaimer, the term of this patent is extended or adjusted under 35 U.S.C. 154(b) by 227 days.

(21) Appl. No.: 09/930,627

(22) Filed: Aug. 16, 2001

(65) Prior Publication Data

US 2003/0035849 A1 Feb. 20, 2003

(51) Int. Cl.⁷ .............................. A61K 7/00; A61K 7/48; A61K 33/14; A61K 33/00; A61K 35/02
(52) U.S. Cl. ................ 424/680; 424/600; 424/617; 424/663; 424/665; 424/667; 424/673; 424/677; 424/678; 424/679; 424/681; 424/682; 424/722; 424/723; 424/401; 424/70.1; 514/844; 514/886; 514/887
(58) Field of Search ................. 424/480, 600, 424/617, 663, 665, 667, 673, 677–679, 681, 682, 722, 723, 401, 70.1; 514/844, 886, 887

(56) References Cited

PUBLICATIONS

Derwent abstract, accession No. 1998–350371; abstracting FR 2757060 (Jun. 1998).*
STN Online, File NLDB, accession No. 2000:265190; abstracting, "Dea sea Products: Coming to life," European Cosmetic Markets, vol. 17(9), Sep. 2000, p. 341.*

\* cited by examiner

Primary Examiner—John Pak
(74) Attorney, Agent, or Firm—Oltman, Flynn & Kubler

(57) ABSTRACT

A reconstituted ocean mixture comprising, sea salt, and the purified product of reverse osmosis of water. A method is provided for treating a pierced area of a person's skin comprising applying to the pierced area a reconstituted ocean water mixture of sea salt and the product of reverse osmosis of water.

1 Claim, 1 Drawing Sheet

TOPICALLY APPLIED SYNTHETIC OCEAN WATER MIXTURE AND METHOD OF USING SAME

BACKGROUND OF THE INVENTION

Field of the Invention

This invention relates to a topically applied reconstituted ocean water mixture for use on/in a person's skin for cleansing and healing and to a method of treating a pierced area of a person's skin using this mixture.

SUMMARY OF THE INVENTION

The present invention is directed to a novel topically applied sea salt mixture whose efficacy and safety are based on its novel composition as well as to a novel method of treating a pierced area of a person's skin with this mixture.

A principal object of this invention is to provide a novel synthetic ocean water mixture whose efficacy and safety for such uses as topical application on pierced skin areas, throat spraying and the like are achieved by virtue of the exceptional purity and sterility of its ingredients.

Another principal object of this invention is to provide a novel method of treating a pierced area of a person's skin by the use of this synthetic ocean water mixture.

Further objects and advantages of the invention will be apparent from the following detailed description of a presently preferred embodiment thereof, illustrated in the accompanying drawing.

DETAILED DESCRIPTION OF THE INVENTION

Figure 1:
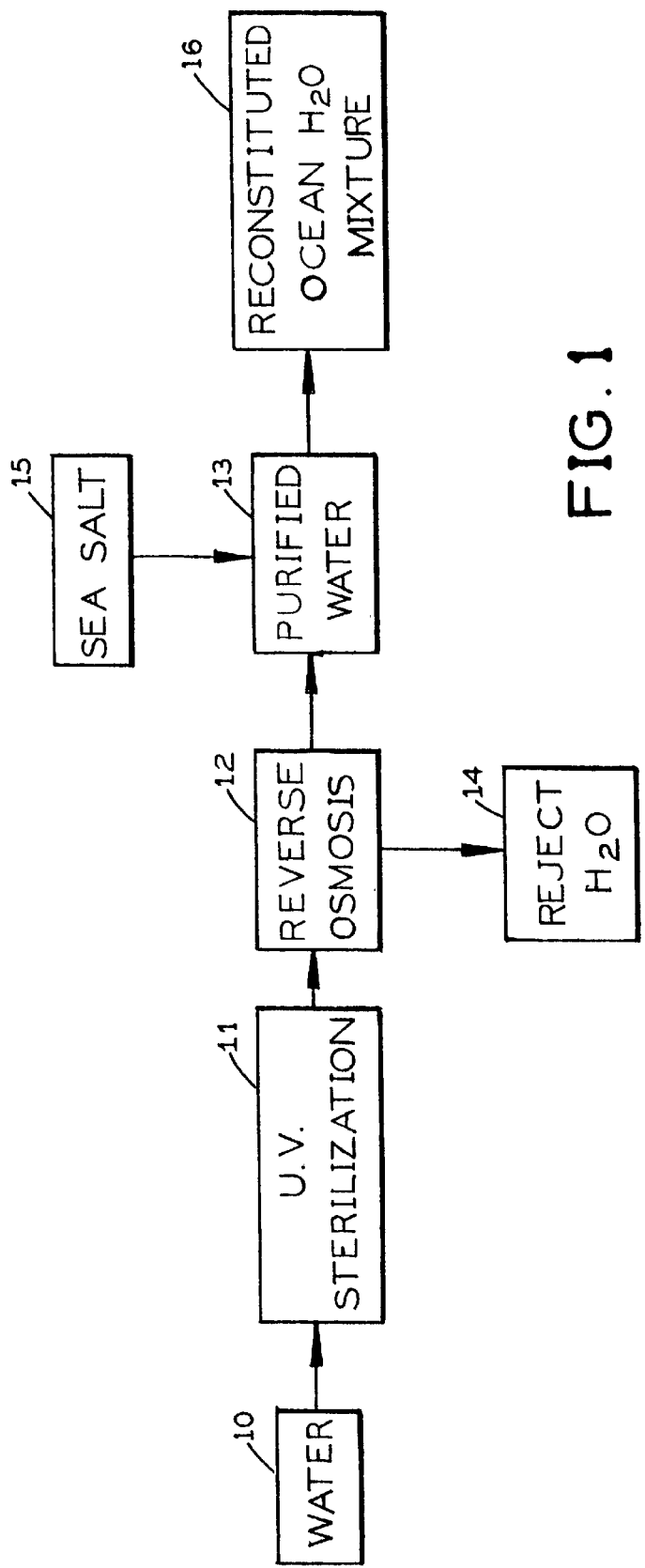
FIG. 1 is a flow chart of the novel process of making the present mixture.

Referring to the drawing, in accordance with the present invention a skin mixture for topical application to a pierced area of a human body, such as one that has been subjected to a body piercing procedure in a tattoo parlor, is prepared by subjecting water 10 to ultraviolet sterilization 11 to reverse osmosis 12 to produce purified water 13 as well as reject water 14 which may be discarded or used for a purpose unrelated to the production of the present reconstituted ocean water mixture. Equipment of known design is used to perform this reverse osmosis. The purified water product 13 of the reverse osmosis operation is then mixed with sea salt 15 to produce a liquid product 16 with a high salt concentration that may be applied topically on the pierced area of the person's skin.

The sea salt 15 in the present mixture is a commercially available product that is recommended by many chefs as a condiment or seasoning to replace common table salt, and it has the purity required for human ingestion. Sea salts minerals and elements are richer and more abundant than those of common table salt. Thus, both components of the present skin treatment mixture—the sea salt and the reverse osmosis purified water are of very high purity to guard against infection or other harm to the wound or the surrounding skin area during the healing process that takes place following a body piercing operation.

The reconstituted ocean water mixture produced as described with reference to FIG. 1 also may be used as a throat spray to cleanse and heal the infected membranes of the pharynx. The reconstituted ocean water formulation can also be used to safely cleanse and heal a variety of other ailments including: tonsillitis, abscessed teeth, infected gums, and canker sores.

Although ocean water is the most abundant substance on the planet (approximately 78%), this invention represents the first attempt ever to reconstitute ocean water by purifying and sterilizing water and then combining the inherent trace elements and minerals which are found in sea salt for the commercial purposes described herein.

We claim:

1. A method of treating a pierced area of a person's skin comprising, applying to the pierced area a reconstituted ocean water mixture of sea salt and the product of reverse osmosis of water.

* * * * *